United States Patent [19]

McReynolds

[11] Patent Number: 5,084,978
[45] Date of Patent: Feb. 4, 1992

[54] DENTAL SAW AND ABRASIVE TOOL

[76] Inventor: William D. McReynolds, 13661 A Ruette Le Parc, Del Mar, Calif. 92014

[21] Appl. No.: 584,776

[22] Filed: Sep. 19, 1990

[51] Int. Cl.$^5$ .............................................. B26B 1/00
[52] U.S. Cl. .............................. 30/517; 30/338; 30/339; 606/82; 606/176
[58] Field of Search ............. 30/329, 337, 338, 339, 30/517, 524, 514, 336, 334, 340; 606/182, 176, 177, 178

[56] References Cited

U.S. PATENT DOCUMENTS

| | | | |
|---|---|---|---|
| 936,474 | 10/1909 | Post | 30/338 |
| 1,031,495 | 7/1912 | Walker | 30/336 |
| 1,242,913 | 10/1917 | Ahlgran | 30/336 |
| 1,284,808 | 11/1918 | Steers | 30/338 |
| 1,325,540 | 12/1919 | Spahr | 30/336 |
| 1,534,310 | 4/1925 | Gaunt | 30/338 |
| 1,584,319 | 5/1926 | Oki | 30/339 |
| 2,172,680 | 9/1939 | Noreau | 30/338 |
| 2,549,229 | 4/1951 | Ottoson | 30/338 |
| 2,599,193 | 6/1952 | Morris | 30/339 |
| 2,752,207 | 6/1956 | Young | 30/517 |
| 3,201,867 | 8/1965 | Case | 30/339 |
| 3,257,726 | 6/1966 | Longobardi | 30/339 |
| 4,021,912 | 5/1977 | Stanfield | 30/338 |

Primary Examiner—Douglas D. Watts
Assistant Examiner—Hwei-Siu Payer
Attorney, Agent, or Firm—Lewis E. Massie

[57] ABSTRACT

A dental tool with detachable saw blades and adhesively affixed abrasive strips on the distal ends of a U shaped handle for removing the solified resin in posterior and anterior teeth during the placement of porcelain and composite inlays while keeping the tongue and cheek away from the cutting surfaces. The primary function of the tool is provided by a finger rest to direct the tool force in a gingival direction with stability and control improving the function and safety of the tool.

1 Claim, 1 Drawing Sheet

DENTAL SAW AND ABRASIVE TOOL

BACKGROUND OF THE INVENTION

1. Field of the Invention

Hand tool made from spring steel, or the like, wherein the handle is bent on itself to arrange converging spring arms the distal ends of which are yieldable to and from each other, are old in the related art. Similar scrapers, choppers and cutters wherein the cutting blades are retained by gripping elements on the distal ends of said handles are likewise old in the related art.

2. Description of the Related Art

Similar hand tools described the related art include: U.S. Pat. No. 2,172,680 Noreau Jr., which describes a novel razor blade handle for razor blades of the Gem-type which is suited to hold the blade in position for use; U.S. Pat. No. 3,201,867 Case, which discloses a hand type tool specially for holding razor blade type scrapers; U.S. Pat. No. 2,599,193 Morris, which discloses a hand held scraping tool wherein a thin scraper blade, of any contour, is supported by a detachable one-piece wire handle.

SUMMARY OF THE INVENTION

The instant invention relates to a compact saw and abrasive tool specifically applied for use by dentists is the removable of solidified rosin in posterior and anterior teeth during the procedure for placement of porcelain and composite inlays, on-lays, and veneers. The form of the tool separates the cheek and tongue from the cutting, or abrasive, members of the tool thus eliminating injuries thereto. The saw is additionally useful in creating ideal interproximal contacts in silver alloy restorations between teeth. With the abrasive blade the tool functions to plane interproximal cervical areas to a smooth debris-free state.

Considerable manual dexterity and operational skill is required to perform the sawing and abrasive functions within the limited confines of a human mouth. Gripping a simple conventional handle does not transmit adequate motion to the saw or abrasive tool. To add additional motion transmittal the handle of the subject tool is equipped with a U shaped receptacle that accommodates a thumb or finger that allows controlled vertical or sideways pressure to the sawing or abrasive action.

The tool handle comprises a bent U shaped member with parallel sides flared inwardly at an intermediate portion thereof. The U shaped member is formed from spring steel or the like, rod. The rod has an approximate diameter of 0.188 inches. The handle relatively elongated, that is the width being less than the length. A finger support receptacle, with parallel side members extending upwards from the plane of the handle, is attached to the approximate longitudinal center of the handle. The distal end of the handle rods curved upwardly from the plane of the handle terminating in extruding pins of a reduced diameter.

The saw blade is a thin rectangular member with center line mounting holes on each end. The diameter of the mounting holes accommodates the 0.100 inch diameter of the extruding pins on the ends of the handle rods. The saw blade does not exceed 0.002 inches in thickness, 0.15 in width, and 1.00 inches in length.

A blade similar to the saw blade but without saw teeth is used to support strips of abrasive material for abrasive applications of the tool.

An important advantage of the instant invention is the all metal construction which can withstand the chemicals and heat associated with conventional sterilizing techniques.

DETAILED DESCRIPTION OF THE PREFERRED EMBODIMENT

Figure 1:
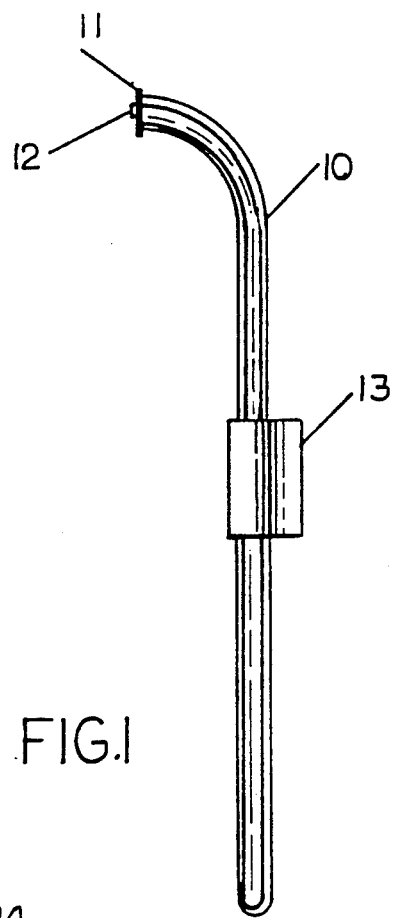
FIG. 1 is a left, side elevation of the dental saw and abrasive tool.

FIG. 1 shows the hand tool 10 with the saw blade 11 fastened to the protruding pins 11 on the distal end ends of the tool handle and the finger receptacle 13.

Figure 2:
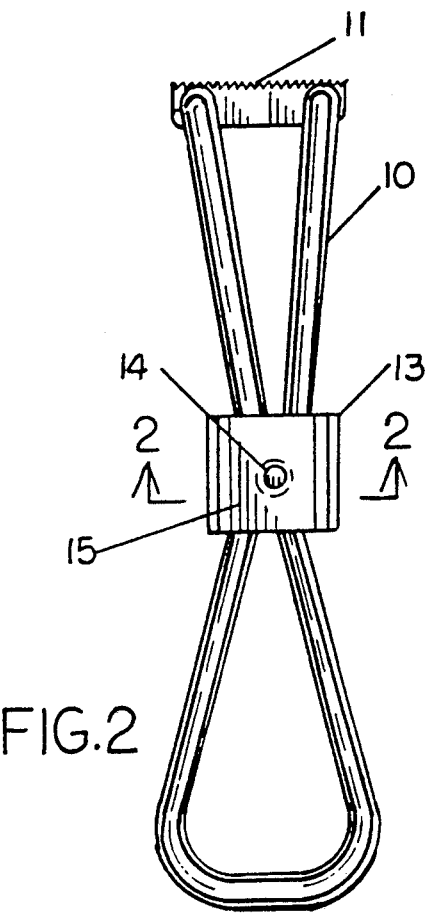
FIG. 2 is a front elevation of the dental saw and abrasive tool.

The front view of FIG. 2 shows the tool handle 10, the saw blade 11, the finger receptacle 15, the fastening rivet 14 and the sides of the finger receptacle 13.

Figure 3:
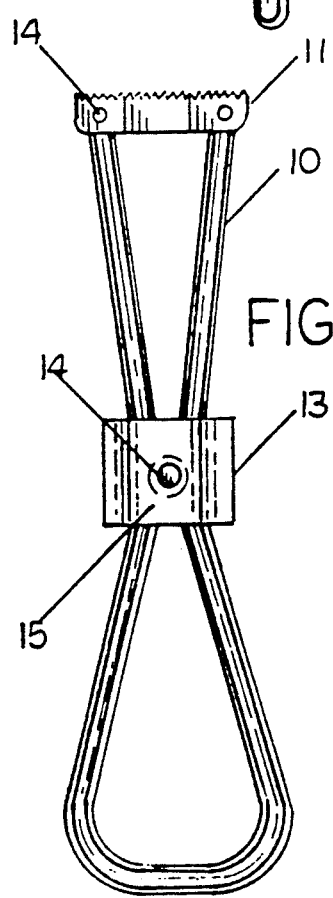
FIG. 3 is a back elevation of the dental saw and abrasive tool.

FIG. 3 is a back elevation of the tool showing the saw blade the finger receptacle 15, the sides of the finger receptacle 13 and the fastening rivet 14.

Figure 4:
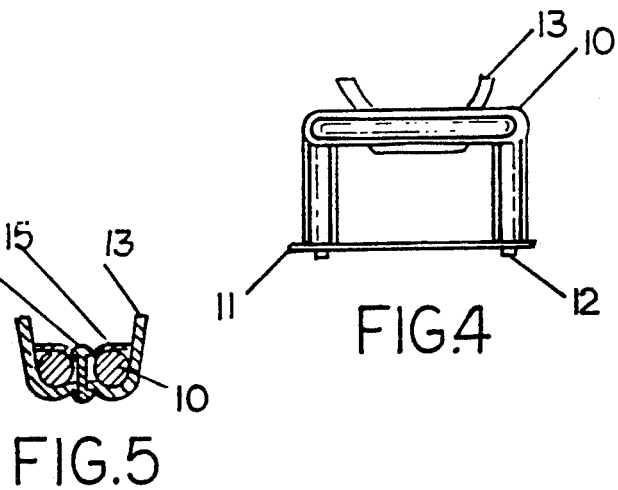
FIG. 4 is a bottom view of the dental saw and abrasive tool.

FIG. 4 shows the tool 10, the upward sides 13 of the finger receptacle 15 and the saw blade 11 mounted on the pins 12.

Figure 5:
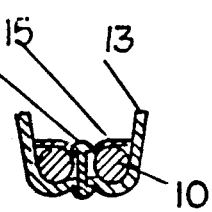
FIG. 5 is a sectional view through 2—2 of FIG. 2.

In FIG. 5 the finger receptacle 15 with sides 13 is shown attached to the handle rods 10 by the rivet 14.

In use the distal ends of the handle 10 which are spread outwardly by the inherent spring action in the spring steel handle rods, are pressed together to accommodate the mounting holes in the saw blade 11. The finger receptacle 15, a primary feature of the instant invention, reacts to finger pressure to direct force of the tool in a gingival direction under optimal control with a one finger rest function to increase stability and force.

I claim:

1. A dental saw and abrasive tool comprising a U shaped handle made of spring steel bent to form a pair of essentially parallel rods said rods having distal end portions bent forward to form a saw support;

said distal end portion of said rods terminating in protruding circular pins of a reduced diameter to that of the rods;

the parallel tool handle rods flared inwardly at approximately the vertical center of the handle;

a thin, narrow, rectangular shaped saw blade with centered mounting holes on each end affixed to the circular protruding pins with the saw teeth facing outwardly;

the inherent spring forces of the rods providing a tension force to secure the saw blade to the tool handle; and the saw blade affixed to the ends of the tool handle rods by compressing the rod end inwardly to accommodate the mounting holes in the saw blade;

the improvement comprises a finger receptacle formed of a U shaped cavity with vertical side walls and a horizontal top wall fixedly attached to the center of the parallel rods for accommodating the manipulation of the tool to achieve a better control of vertical and side pressure on the tool when it is held in an operator's hand.

* * * * *

UNITED STATES PATENT AND TRADEMARK OFFICE
Certificate

Patent No. 5,084,978

Patented: February 4, 1992

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: William D. McReynolds, Del Mar, CA; and Frank A. Samuelsson, Redwood City, CA.

Signed and Sealed this Twenty-ninth Day of April 2003.

RICHARD K. SEIDEL
*Supervisory Patent Examiner*
Art Unit 3204